United States Patent
Nishio et al.

(10) Patent No.: US 9,005,970 B2
(45) Date of Patent: Apr. 14, 2015

(54) METHOD OF CULTURING CELLS UNDER REGULATION IN THE EXTENSION DIRECTION

(75) Inventors: Ryosuke Nishio, Kyoto (JP); Taiji Nishi, Chiyoda-ku (JP); Motohiro Fukuda, Tsukubi (JP); Yasuzo Kirita, Kurashiki (JP); Seiichi Kanai, Tsukuba (JP); Takenori Kitani, Tsukuba (JP)

(73) Assignees: Kuraray Co., Ltd., Kurashiki-shi (JP); Ryosuke Nishio, Kyoto (JP)

( * ) Notice: Subject to any disclaimer, the term of this patent is extended or adjusted under 35 U.S.C. 154(b) by 1220 days.

(21) Appl. No.: 11/813,720

(22) PCT Filed: Jan. 11, 2006

(86) PCT No.: PCT/JP2006/300184
§ 371 (c)(1),
(2), (4) Date: Apr. 10, 2008

(87) PCT Pub. No.: WO2006/075597
PCT Pub. Date: Jul. 20, 2006

(65) Prior Publication Data
US 2009/0017540 A1    Jan. 15, 2009

(30) Foreign Application Priority Data
Jan. 11, 2005    (JP) .................................. 2005-003926

(51) Int. Cl.
*C12M 1/12*    (2006.01)
*C12M 1/32*    (2006.01)
(Continued)

(52) U.S. Cl.
CPC ............... *C12M 25/06* (2013.01); *C12M 23/12* (2013.01); *C12N 2533/30* (2013.01)

(58) Field of Classification Search
CPC .............................. C12M 25/06; C12M 23/12
USPC ....................................... 435/305.2, 383, 395
See application file for complete search history.

(56) References Cited

U.S. PATENT DOCUMENTS

| | | | |
|---|---|---|---|
| 6,448,069 B1 * | 9/2002 | Cecchi et al. | 435/305.2 |
| 2003/0232431 A1 * | 12/2003 | Law | 435/366 |
| 2005/0084512 A1 * | 4/2005 | Denizeau et al. | 424/423 |

FOREIGN PATENT DOCUMENTS

| | | |
|---|---|---|
| JP | 2004 154027 | 6/2004 |
| JP | 2006 50975 | 2/2006 |

OTHER PUBLICATIONS

English translation of Teruo et al. (JP 2004-154027).*
(Continued)

*Primary Examiner* — Nathan Bowers
*Assistant Examiner* — Gautam Prakash
(74) *Attorney, Agent, or Firm* — Oblon, McClelland, Maier & Neustadt, L.L.P.

(57) ABSTRACT

[PROBLEMS] Relating to a bioassay method with the use of cultured cells and cell culture for a therapeutic purpose in the case of determining the efficacy of a drug or the like or examining the toxicity thereof, it is intended to provide a method of culturing cells under regulation in the extension direction and a cell culture plate. [MEANS FOR SOLVING PROBLEMS] A cell culture plate having a plural number of side walls (1) and a plural number of space structures (3) for providing cultured cells which are formed by the side walls (1), wherein the side walls (1) are provided with openings (2) so that the space structures (3) are linked together. By using this cell culture plate, a method of culturing cells under regulation in the extension direction can be provided.

19 Claims, 6 Drawing Sheets

(51) Int. Cl.
*C12N 5/02* (2006.01)
*C12M 1/22* (2006.01)

(56) References Cited

OTHER PUBLICATIONS

Shimizu et al., Cell sheet engineering for myocardial tissue reconstruction, Biomaterials 24, 2309-2316 (2003).*

Kojima et al., "A novel method of cultivating cardiac myocytes in agarose microchamber chips for studying cell synchronization", J. Nanobiotechnol. 2(9), 2004.*

U.S. Appl. No. 12/665,474, filed Dec. 18, 2009, Tazaki, et al.
U.S. Appl. No. 13/229,087, filed Sep. 9, 2011, Tazaki, et al.

* cited by examiner

TOP VIEW

SIDE VIEW

METHOD OF CULTURING CELLS UNDER REGULATION IN THE EXTENSION DIRECTION

CROSS-REFERENCE TO RELATED APPLICATIONS

This application is a National Stage of PCT/JP06/300184 filed Jan. 11, 2006 and claims the benefit of JP 2005-003926 filed Jan. 11, 2005.

TECHNICAL FIELD

The present invention relates to a method of culturing cells for use in a bioassay using cultured cells for evaluating the efficacy of a drug or the like or in examining the toxicity thereof or for a therapeutic purpose.

BACKGROUND ART

The technique using cells isolated from a tissue in testing or examination is now an essential method in the biotechnology-related fields. It is widely used in diagnosing a disease or morbid condition, searching for a new drug and evaluating the efficacy of a drug, or in animal inspection, plant inspection and testing for environment pollutants, among others.

The cells isolated are sometimes immediately subjected to testing but, in many cases, they are cultured in culture dishes or test tubes in the manner of cell culture. Various assays are carried out in such culture systems.

Generally, in these assays, a uniform culture system is established and, for example, the amount or concentration of a drug or the like to be evaluated in that system is varied to estimate the effect thereof. Therefore, the culture vessels used for such culture are made uniform and constant in shape. As the culture vessels, use is generally made of the so-called culture dishes or plates.

Generally used as such culture dishes or plates are petri dishes and 6-well, 12-well, 48-well and 96-well plates (cf. Patent Document 1). In response to the recent trend toward miniaturization, the use of 384-well plates smaller in well diameter and increased in the number of culture wells has also been started.

However, when the culture of tissue cells is carried out in those cell culture dishes or plates which are commercially available, there arises a problem that cells extend thinly to take a form showing no directionality and no longer show one or more functions they have in vivo.

For confirming certain cell activities, it is possible to measure the change in pH due to discharge of a waste material or the level of carbon dioxide emission by means of an electrochemical sensor, for instance. Attempts have been made to compare the measured data for a vital tissue with the measured data for cells cultured on culture dishes or plates. Under present conditions, however, the values reproducing the data for vital tissues cannot be reproduced on culture dishes or plates. A plausible reason is that while each plate well has a vessel-like form, it means nothing but plate culture to cells several microns to several tens of microns in size. In particular, in the case of proliferation of tissue cells such as hepatocytes which are difficult to culture, it becomes more difficult to allow them to function as in vivo.

As a means for solving such problems, an attempt has been made to form, on culture plates, a fine vessel pattern suited for the growth of tissue cells and culture cells within such fine vessel pattern (cf. Patent Document 2). Namely, it is intended to culture cells in each fine vessel pattern to propagate cells three-dimensionally so that they may perform a function(s) they have in vivo.

Currently, however, this means can be applied only to cell culture for certain bioassays or for certain therapeutic purposes alone. For example, cardiac myocytes of a living individual beat in response to an electric signal transmitted from the brain. For performing their pulsating function, cardiac myocytes in a living body are constituted so that the arrangement thereof may have directionality. Therefore, in the field of biotechnology, tissue culture under regulation of the extension direction, like in the case of living tissues, is required in studying tissue regeneration in artificial organs. To the contrary, the culture on the conventional culture plates has a problem that, in addition to the difficulty of three-dimensional culture, it cannot regulate the extension direction, so that it cannot be applied for purposes of research and testing.

As an example of cardiac muscle culture for a therapeutic purpose, transplantation of a cultured cardiac muscle tissue partly into the cardiac muscle tissue necrotized by cardiac infarction for lifesaving has been studied. The whole heart pulsates greatly in response to an electric signal from the brain. Upon necrosis of a part of the cardiac muscle tissue due to myocardial infarction, the signal transduction within the cardiac muscle is blocked, with the result that the heart repeats small contractions called fibrillation. Accordingly, thrombi are formed as a result of residence of blood in the heart and, in the case of their being carried to the brain tissue, such a secondary case as cerebral infarction may be induced. Prolonged fibrillation may possibly lead to death. In the treatment of such condition, the object is not the completion of an artificial organ but the substitution of a part of the tissue. Therefore, it is desired that such cardiac tissue culture be realized as early as possible.

Under the existing circumstances, however, the culture on the conventional culture plates cannot regulate the extension direction, in addition to the difficulty in three-dimensional culture, hence has a problem that it cannot be applied for this purpose, either.

Patent Document 1: Japanese Kokai (Laid-open) Publication H11-169166
Patent Document 2: Japanese Kokai Publication

DISCLOSURE OF INVENTION

Problems which the Invention is to Solve

In cell culture for the purpose of bioassaying using cultured cells in evaluating the efficacy of a drug or the like or testing the same for toxicity or for a therapeutic purpose, those culture plates which are commercially available have a problem in that cells extend thinly without showing any directionality and fail to show their function(s) they have in vivo. The attempt to form, on a culture plate, a fine vessel pattern suited for the proliferation of tissue cells and culture cells within that fine vessel pattern also has a problem that the extension direction cannot be regulated, and therefore, the technique cannot be applied to the culture of cardiac myocytes for a therapeutic purpose.

The present invention, which has been completed to solve such problems, has for its object to provide a method of culturing cells under regulation of the direction of extension of cultured cells and a cell culture plate for use in practicing the method of culturing cells.

Means for Solving the Problems

To solve the above problems, the present invention provides a method of culturing cells characterized in that a cell culture plate having plural side walls and plural space structures for arranging cultured cells which are formed by the side walls, and having a communicative structure resulting from providing the side walls with openings for communication of the plurality of space structures among them is used to thereby induce the formation of desmosomes, which serve as pseudo-scaffolds in cell culture, on the side walls, whereby cells cultured in each space structure extend toward the opposing side walls and the cells cultured in the respective space structures are connected through the openings and thus the direction of extension of cultured cells is regulated.

The invention also relates to a method of culturing cells as described above, in which each side wall in the cell culture plate has a height of 3 μm to 1000 μm, a thickness of 3 μm to 1000 μm and a width of 3 μm to 3000 μm. It further relates to a method of culturing cells as described above, in which the cell culture plate has a channel or channels for the perfusion of a culture solution and the channel width is 1 μm to 1000 μm and the channel depth is 1 μm to 1000 μm.

Further, the invention relates to a method of culturing cells as described above, in which the cell culture plate has a fine uneven or rugged pattern with each projection or cavity being 0.001 μm to 50 μm in height or depth, respectively, within each space structure for arrangement of cells.

In another aspect, the invention provides a method of culturing cells characterized in that a cell culture plate having plural concave or convex patterns and having a surface communicating with the upper part of each concave or the bottom of each convex as a result of providing such concave or convex patterns is used to thereby induce the formation of desmosomes, which serve as pseudo-scaffolds in cell culture, on the communicating surface or on the side walls of each rugged pattern, whereby cells grow on the communicating surface where they can extend and thus the direction of extension of cultured cells is regulated.

On the other hand, the invention provides a cell culture plate having plural side walls and plural space structures for arranging cultured cells which are formed by the side walls, and further having a communicative structure resulting from providing the side walls with openings for communication of the plurality of space structures among them as well as a cell culture plate having plural concave or convex patterns and having a surface communicating with the upper part of each concave or the bottom of each convex as a result of providing such concave or convex patterns.

In a further aspect, the cell culture plate of the invention is surface-treated for cell immobilization. In a further aspect, the cell culture plate of the invention is made of a resin molding. In a still further aspect, the cell culture plate of the invention is one in which the resin molding is a water-soluble resin molding.

In a further aspect, the invention provides a multilayer plate for cell culture comprising plural cell culture plates as mentioned above resulting from lamination.

Effects of the Invention

The present invention relates to a method of culturing cells under regulation of the extension direction for a bioassay using cultured cells for evaluating the efficacy of a drug or the like or in examining the toxicity thereof or for a therapeutic purpose.

When the method of the invention is applied, for example, to the case where the cardiac muscle tissue is partially necrotized due to cardiac infarction and, as a result, the signal transduction within the cardiac muscle is blocked and the heart is in the condition of fibrillation, it becomes possible to transplant a tissue consisting of cardiac myocytes regulated in the extension direction and thereby recover the signal transduction within the heart muscle and regain normal pulsation of the heart.

EXPLANATION OF SYMBOLS

Figure 1:
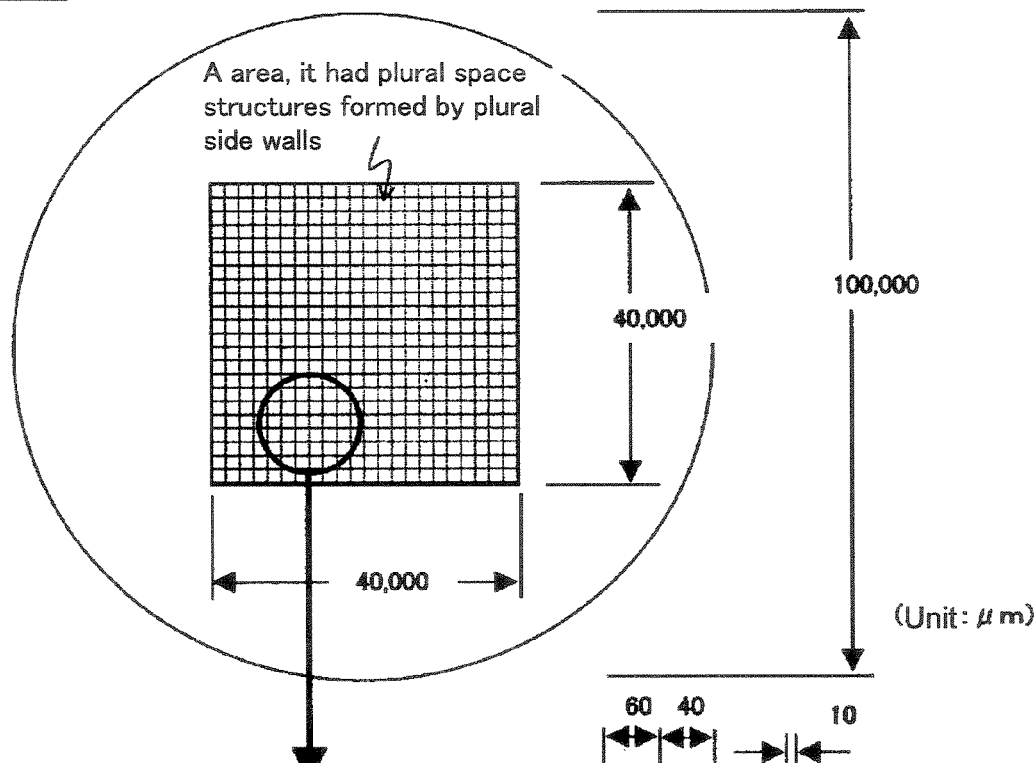
FIG. 1 A representation of an example of the embodiment of the cell culture plate.
Figure 1:
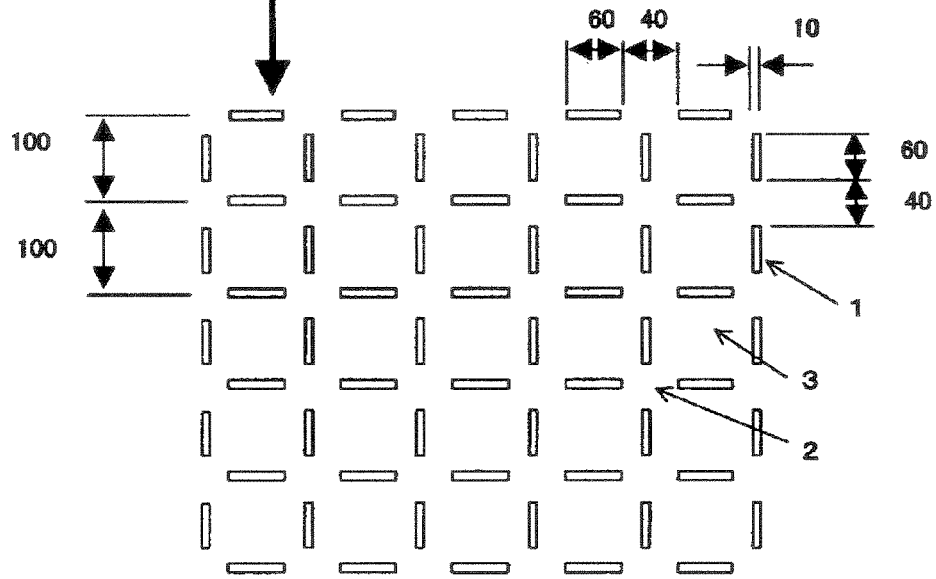
Figure 1:
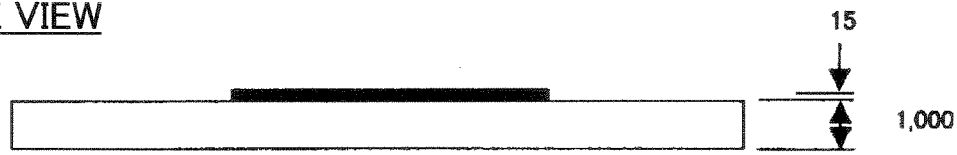

1: side wall, 2: opening, 3: space structure, 4: through-hole, 5: channel, 6: concave pattern, 7: communicating surface.

BEST MODES FOR CARRYING OUT THE INVENTION

In the following, the present invention is described in detail.

When tissue cell culture is carried out on commercially available cell culture dishes or plates (petri dishes or well plates), cultured cells extend thinly and take a form having no directionality. Researchers have attempted to compare the data obtained by measurement of the change in pH due to waste material discharge or of the carbon dioxide emission by means of an electrochemical sensor or the like with the measured data for cells cultured on a culture plate, as means for cell activity confirmation. At the present, however, the data shown by a living tissue cannot be reproducibly obtained on culture plates. Therefore, it is judged that cultured cells as cultured on the commercially available cell culture plates fail to show their function(s) they have in vivo. Thus, researches have just been started for forming, on a culture plate, a fine vessel pattern suited for the growth of tissue cells and culturing cells in the fine vessel pattern to allow three-dimensional cell growth so that the function(s) the cells have in vivo may be manifested.

However, even if it is intended that a tissue consisting of cells cultured of a culture plate having a fine vessel pattern be actually applied for a therapeutic purpose, there is a great obstacle under the existing circumstances to the application thereof for therapeutic use even when it becomes possible to culture cells three-dimensionally, because the structure of a tissue consisting of cultured cells is not the same as the structure in a living organism. For example, in applying to the case where the cardiac muscle tissue is partially necrotized due to cardiac infarction and, as a result, the signal transduction within the cardiac muscle is blocked and fibrillation of the heart is caused thereby, it is only a tissue consisting of cardiac myocytes regulated in the extension direction that can restore the signal transduction in the cardiac muscle and regain normal pulsation of the heart.

According to the method of culturing cells as provided by the present invention, it becomes possible, by use of a cell culture plate having plural side walls and plural space structures for arranging cultured cells which are formed by the side walls and further having a communicative structure resulting from providing the side walls with openings for communication of the plurality of space structures among them, to realize three-dimensional growth and, in addition, regulate the direction of extension of cultured cells and thus obtain a tissue identical to the corresponding vital tissue and with a desired area and a desired thickness as a result of interconnection of cells cultured in the respective space structures. Thus, cultured tissues desired by researchers in the fields of medicine and medical engineering as well as by patients can be realized.

By having plural side walls, plural space structures are constructed, and the area size of the space structures is selected according to the intended use. The required and applicable total size of the plurality of space structures is 0.5 mm to 30 mm in length and at least 1 mm to 20 cm in width.

In the cell culture, focal adhesion, which is a site of adhesion to the scaffolds, are formed on the side walls, and cells grow three-dimensionally each space and form a skeletal structure. The desmosomes of cells that have extended to the opposing side walls in the respective space structures are mutually connected through the openings, whereby it becomes possible to produce a cultured tissue regulated in the extension direction.

By selecting the sizes of the side walls, space structures and openings according to the cell species to be cultured, it supposedly becomes possible to regulate the extension direction in various culture systems. The term "openings" indicates a structure allowing the mutual communication of the space structures formed by the side walls. For example, gaps or intervals between the side walls, concave structures on the side walls, or tunnel structures formed in the side walls are also effective as the openings for cell-cell adhesion.

It is important that the size of the side walls and the size of the space structures formed by the side walls in the cell culture plate be each within a range optimal for the purpose of cell culture. If the space structures formed by the side walls are excessively large, cells will extend thinly and show no three-dimensional structure, as in the case of plate culture, hence the direction of extension thereof cannot be regulated. If the space structures are excessively small, it will become impossible for cells to enter the space structures Therefore, the size of the space structures is desirably in such a range that each space structure can contain one single cell or plural cells according to the cell species to be cultured.

The side wall height is preferably within the range of 3 µm to 1000 µm, more preferably 5 µm to 500 µm. The thickness is preferably within the range of 3 µm to 1000 µm, more preferably 5 µm to 500 µm. The width is preferably 3 µm to 3000 µm, more preferably 5 µm to 1000 µm.

The channel or channels for causing a culture solution to flow through the same are now described. One of the objects of the channel(s) for causing a culture solution to flow through the same is to always feed a fresh culture solution to cells to thereby prevent the culture solution from becoming less fresh due to wastes discharged by cells and thus prevent cells from becoming incapable of showing the function(s) thereof they have in vivo.

Further, the channel or channels for causing a culture solution to flow through the same are expected to make it possible to regulate the direction of extension of cultured cells in the culture plate. When the rate of flow and the space for the flow of the culture solution, among others, are properly selected, the culture solution imposes a shearing stress on cultured cells, and this shearing stress can supposedly make it possible to regulate the direction of extension of cultured cells.

The channel or channels for causing a culture solution to flow through the same can also play a role in recovering a product(s) produced by cultured cells and optionally feeding the same to another series of media. It is also possible to recover the product(s) through a minute fluid connector or connectors provided along the channel(s) or at the end(s) of the channel(s) for utilization in new drug development or for realizing a model close to the vital tissue by feeding the same to another culture plate. As for the shape of the channel(s), any shape can be employed provided that the culture solution feeding is possible. For example, after bringing a surface having plural space structures of the cell culture plate into close contact with a substrate, the space between the whole of the surface having the space structures and the substrate may be used as the channel for causing a culture solution to flow through the same.

By rendering the width or depth of the channel(s) minute, it becomes possible to obtain a high-density cell culture plate. It is desirable, however, that the width or depth be appropriately selected to secure a sufficient feed amount of a culture solution. From the viewpoint of enabling culture solution feeding and realizing an efficient and integrated cell culture plate, the substantial width or depth of the channel(s) is preferably 1 µm to 1000 µm, more preferably 3 µm to 500 µm. It is possible to provide the above channel(s) between neighboring blocks of plural assembled blocks each comprising plural space structures.

In each space structure for culturing cells, the wall portion of each side wall or the bottom of each space structure, for instance, may have a fine rugged or concave/convex structure for promoting the growth of cells within the space structure. The presence of the above fine concave/convex pattern facilitates the formation of desmosomes which are necessary for immobilization of cells and called pseudo-scaffolds, making it possible to promote the cell differentiation and proliferation. The height or depth of the concave/convex pattern is preferably within the range of 0.001 µm to 50 µm, more preferably 0.005 µm to 25 µm. The lengthwise or transverse size of the fine rugged pattern is preferably within the range of 0.001 µm to 50 µm, more preferably 0.005 µm to 25 µm.

As the technique for forming a rugged pattern not exceeding 1 µm in height, there may be mentioned, for example, sand blast treatment and, for forming a finer rugged pattern, there may be mentioned Ar (argon) plasma etching treatment, among others.

As for the technique for forming a rugged pattern exceeding 1 µm in height, the application of dry etching, wet etching or the like to silicon materials or glass materials is expectedly useful. As for the formation of such pattern, the technique of extrusion molding, injection molding, hot embossing, nano-printing, blow molding, calender molding, cast molding or press molding, for instance, may be employed.

The use of a cell culture plate having plural concave or convex patterns and further having a surface communicating with the upper part of each concave pattern or the bottom of each convex pattern can be expected to be effective in regulating the direction of extension of cultured cells.

When cell culture is carried out using a cell culture plate having plural concave patterns, it becomes possible to culture cells only on those upper parts of the cavities in the concave patterns which are in communication. When the concave pattern bottom area is wide, cultured cells can extend onto the bottom part as well and, therefore, it is preferred that the lengthwise size or the transverse size of the concave pattern bottom or both be within the range of 1 µm to 500 µm. By selecting the lengthwise size of the concave pattern bottom alone within the range of 1 µm to 500 µm and selecting 1 mm, 10 mm or 50 mm as the transverse size thereof in the culture of neurocytes or vascular endothelial cells, for instance, it becomes possible to realize the desired length of cultured cells according to the intended purpose.

When cell culture is carried out using a cell culture plate having plural convex patterns, it is expected that cells be cultured on those bottom parts of the projections in the convex patterns which are in communication. When the convex pattern upper part area is wide, cells cultured may extend onto the upper part as well and, therefore, it is preferred that the lengthwise size or the transverse size of the convex pattern top or both be within the range of 1 µm to 500 µm. By selecting the lengthwise size of the convex pattern top alone within the range of 1 µm to 500 µm and selecting 1 mm, 10 mm or 50 mm as the transverse size thereof in the culture of neurocytes or vascular endothelial cells, for instance, it becomes possible to realize the desired length of cultured cells according to the intended purpose.

The concave or convex pattern depth or height is required for cells to recognize the concavity or convexity and is preferably within the range of 1 µm to 500 µm.

Desmosomes to serve as pseudo-scaffolds in cell culture are formed on the communicating surface or on the rugged pattern side wall surfaces, and cells propagate on the communicating surface on which they can extend, whereby the extension direction can be regulated.

The cell culture plate after fine structure processing is preferably subjected to surface treatment to eliminate bubbles and facilitate cell immobilization. For eliminating bubbles and allowing a culture solution to come into contact with the substrate surface, it is effective to render the substrate surface hydrophilic. Various methods can be applied as the method of surface treatment for rendering the substrate surface hydrophilic. Mention may be made, for example, of the methods utilizing low-temperature plasma treatment, corona discharge treatment and the like, the method comprising applying, for coating, a hydrophilic high-molecular material dissolved in an aqueous solution, vapor deposition polymerization and plasma polymerization, among others. Further, the method comprising grafting a coating material onto functional groups on the substrate surface is known as means for increasing the resistance of the coated high-molecular material against dissolution in the culture solution.

For cell immobilization, mention may be made of the method comprising rendering the substrate surface hydrophobic, forming an inactive metal layer on the surface or applying collagen which is a protein promoting the adhesion of cells, or the like. As the method of rendering the surface hydrophobic, there may be mentioned, for example, the formation of a hydrophobic metal layer by sputtering or vapor deposition, and the formation of a high-molecular material layer by vapor deposition polymerization or plasma polymerization. For the inactive metal layer formation, there may be mentioned, for example, gold vapor deposition or sputtering. On the occasion of surface treatment, any arbitrary portion(s) alone may be modified by covering the other portion(s).

A plastic material is suited as the material to be used in making the culture plate from the surface treatment efficiency viewpoint. When the process of cell growth is to be observed using, for example, a fluorescence microscope, a transparent material enabling transmitted light observation is preferred. The resin material is not particularly restricted but there may be mentioned, for example, acrylic resins, poly(lactic acid), poly(glycolic acid), styrenic resins, acrylic-styrene copolymer resins (MS resins), polycarbonate resins, polyethylene terephthalate and like polyester resins, polyvinyl alcohol resins, ethylene-vinyl alcohol copolymer resins, styrenic elastomers and like thermoplastic elastomers, vinyl chloride resins, polydimethylsiloxane and like silicone resins, vinyl acetate resins (EXEVAL™) and polyvinyl butyral resins, among others.

Suitable as the molding method is the method of forming resin moldings using a metal structure as a mold. The method of forming resin moldings is not particularly restricted but, for example, there may be mentioned injection molding, press molding, monomer cast molding, solvent cast molding, and roll transfer by injection molding, among others. From the productivity and mold shape transferability viewpoint, injection molding is preferably employed. When resin moldings are formed by injection molding using a metal structure selected according to predetermined dimensions as a mold, it is possible to reproduce the shape of the metal structure in the resin moldings with a high level of transferability. The transferability can be confirmed using an optical microscope, scanning electron microscope (SEM) or transmission electron microscope (TEM), for instance.

These resins may contain one or two or more of such additives as lubricants, light stabilizers, heat stabilizers, antifogging agents, pigments, flame retardants, antistatic agents, mold release agents, antiblocking agents, ultraviolet absorbers, and antioxidants.

By recovering the cultured cell tissue alone by peeling off from the cell culture plate after cell culture, it becomes possible to dramatically expand the range of use of the cultured cells. When cultured cells remain immobilized on the substrate, the field of their use is limited to study or testing purposes, for example assaying for toxicity estimation; for medical uses, in particular for application for a therapeutic purpose, it is the limit to the utility of the cell culture plate to use the same as a substitute for an artificial dialysis module, for instance, and it is impossible to utilize them for a therapeutic purpose, for example for restoring a necrotized cardiac muscle tissue by transplantation. Further, if cells are damaged on the occasion of peeling off the cultured tissue, the tissue cannot be used for a transplantation purpose any longer.

By preparing the cell culture plate as a water-soluble resin molding, it becomes possible to peel off the cultured tissue without damaging cultured cells. The cell culture plate is produced from a water-soluble resin and then the surface thereof is coated with collagen, which is a protein promoting the adhesion of cells, for instance. As a result of coating with collagen, cells display sufficient adhesion behavior and proliferate. After culturing cells, it is possible to recover the cultured cells alone by immersing the substrate as such in the culture solution. For example, by raising the culture solution temperature to thereby increase the solubility of the water-soluble resin, it becomes possible to speedily recover the tissue after cell culture. As the water-soluble resin, there may be mentioned poly(lactic acid), poly(glycolic acid), polyvinyl alcohol resins, ethylene-vinyl alcohol copolymer resins, polydimethylsiloxane and like silicone resins, vinyl acetate resins (EXEVAL™, products of KURARAY CO., LTD.), and polyvinyl butyral resins, among others.

By use of a laminated structure made of plural cell culture plates, it becomes possible to carry out plural cell cultures simultaneously and thus efficiently provide culture plates suited for bioassaying.

By use of a laminated structure made of plural cell culture plates, it becomes possible to provide a functional substitute for an artificial dialysis module, for instance. It is expected that the dialyzing function is enhanced by producing a multilayer cell culture plate by lamination of plural cell culture plates and, thus, the efficiency of removal of wastes is increased so that the patient's life may be prolonged.

Also in the case of hepatocytes being the target, it is expected, by culturing Kupffer cells, epidermal cells and so forth separately in plural plate layers, that the resulting cultured cells be useful in the treatment using the same as an artificial liver module or in new drug development utilizing such a product as albumin.

In the case of development of the culture plate for a medical use, in particular for a therapeutic purpose, it is expected, by use of a laminate structure made of plural cell culture plates, that the resulting cultured tissue may be applicable, for example, to a disease accompanied by fabrication as caused by failure in normal pulsation due to partial necrosis of the relevant tissue by myocardial infarction. When a water-soluble resin is used as the cell culture plate material and cell culture is carried out using a laminate structure comprising plural cell culture plates and the substrate is dissolved in the culture solution, it becomes possible to obtain a transplantable stratified heart muscle tissue sheet.

EXAMPLES

In the following, referring to the drawings, the method of regulating the direction of extension of cultured cells and certain shapes according to the invention are described. The following examples illustrate the present invention specifically. These examples are, however, by no means limitative of the scope of the invention.

<Production of Cell Culture Plate A>

A resin molding was formed using a metal structure as a mold. Thus, the metal structure was produced by preparing a resist pattern by photolithography using UV radiation as an exposure light source and depositing a 500-Å-thick nickel layer on the surface thereof by sputtering, followed by electroplating. A 0.5-mm-thick nickel-made metal structure was thus obtained.

Then, the nickel-made metal structure was fixed to the cavity of a mold for molding and a resin-made cell culture plate (A) shown in FIG. 1 was produced by injection molding. The material used for the injection molding was Kuraray's acrylic resin (Parapet G-HS).

The external shape of the cell culture plate A was defined by a substrate having a diameter of 100 mm and a thickness of 1 mm, and the central area, 40 mm in length×40 mm in width, was structured such that it had plural space structures 3 formed by plural side walls 1. Each side wall 1 had a thickness of 10 μm, a height of 15 μm and a width of 60 μm, and each space structure 3, 100 μm in length×100 μm in width and 15 μm in height, was formed by four side walls 1. Each opening 2 for communicating the plurality of space structures 3 was a space or gap between straightly arranged side walls in each of the longitudinal and transverse directions, with the side wall-to-side wall distance being 40 μm.

While this molded article had a flat plate shape, a plate having plural space structures 3 formed by plural side walls may be stuck to the bottom of a petri dish, for instance, so that the study efficiency may be increased.

<Production of Cell Culture Plate B>

Figure 2:
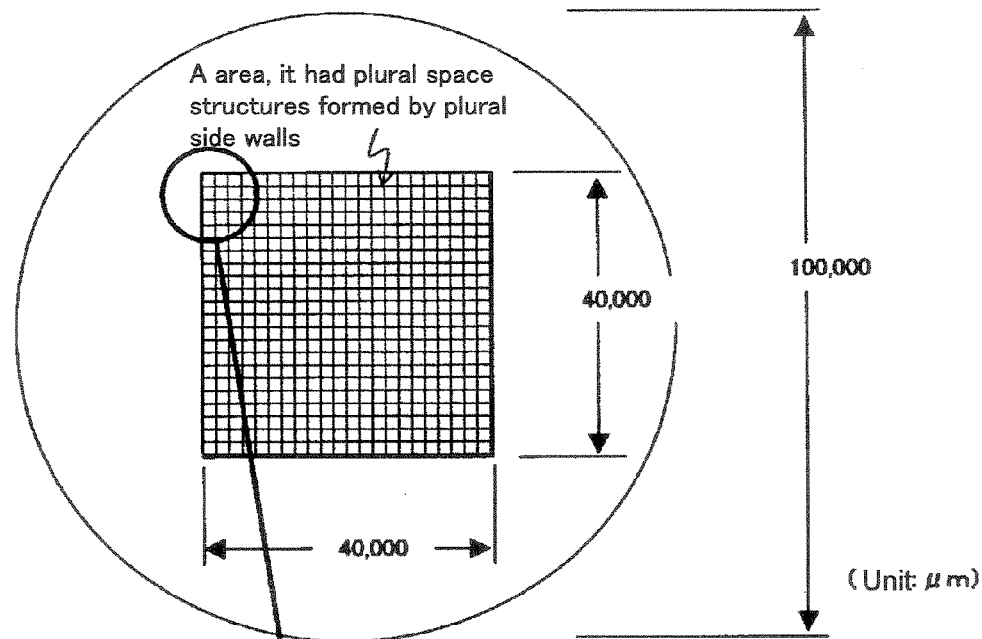
FIG. 2 A representation of another example of the embodiment of the cell culture plate.
Figure 2:
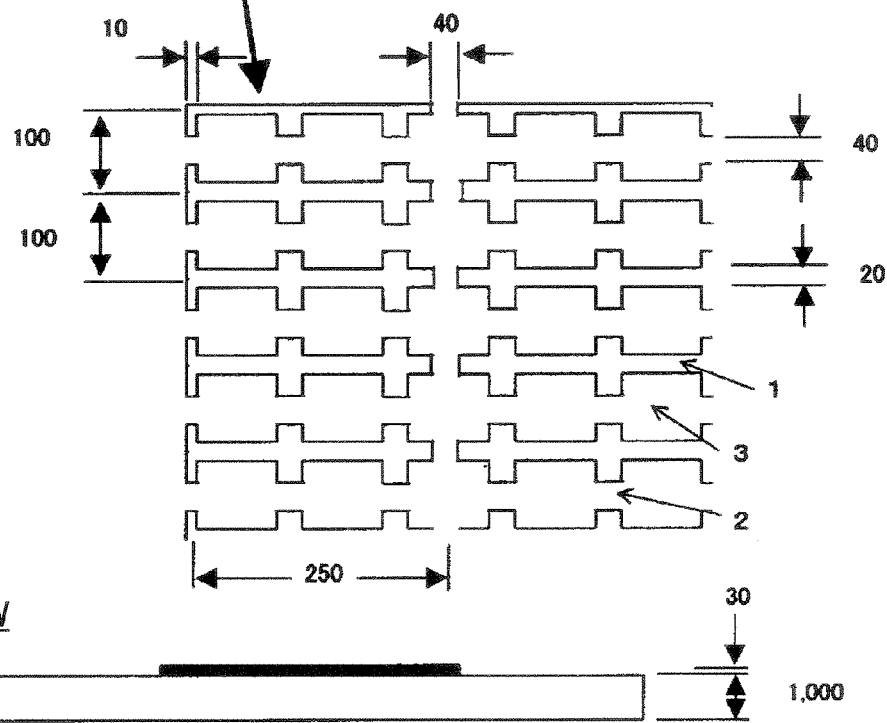

A resin-made cell culture plate (B) shown in FIG. 2 was produced by the same production method as the method of producing the resin-made cell culture plate A.

The external shape of the cell culture plate B was defined by a substrate having a diameter of 100 mm and a thickness of 1 mm, and the central area, 40 mm in length×40 mm in width, was structured such that it had plural space structures 3 formed by plural side walls 1. Each side wall 1 had a thickness of 10-20 μm, a height of 30 μm and a width of 250 μm, and each space structure 3, 100 μm in length×100 μm in width and 30 μm in height, was formed by side walls 1. Openings 2 for communicating the plurality of space structures 3 were obtained with the side wall 1-to-side wall 1 distance being 40 μm.

While this molded article had a flat plate shape, a plate having plural space structures 2 formed by plural side walls 1 may be stuck to the bottom of a petri dish, for instance, so that the study efficiency may be increased.

<Production of Cell Culture Plate C>

Figure 4:
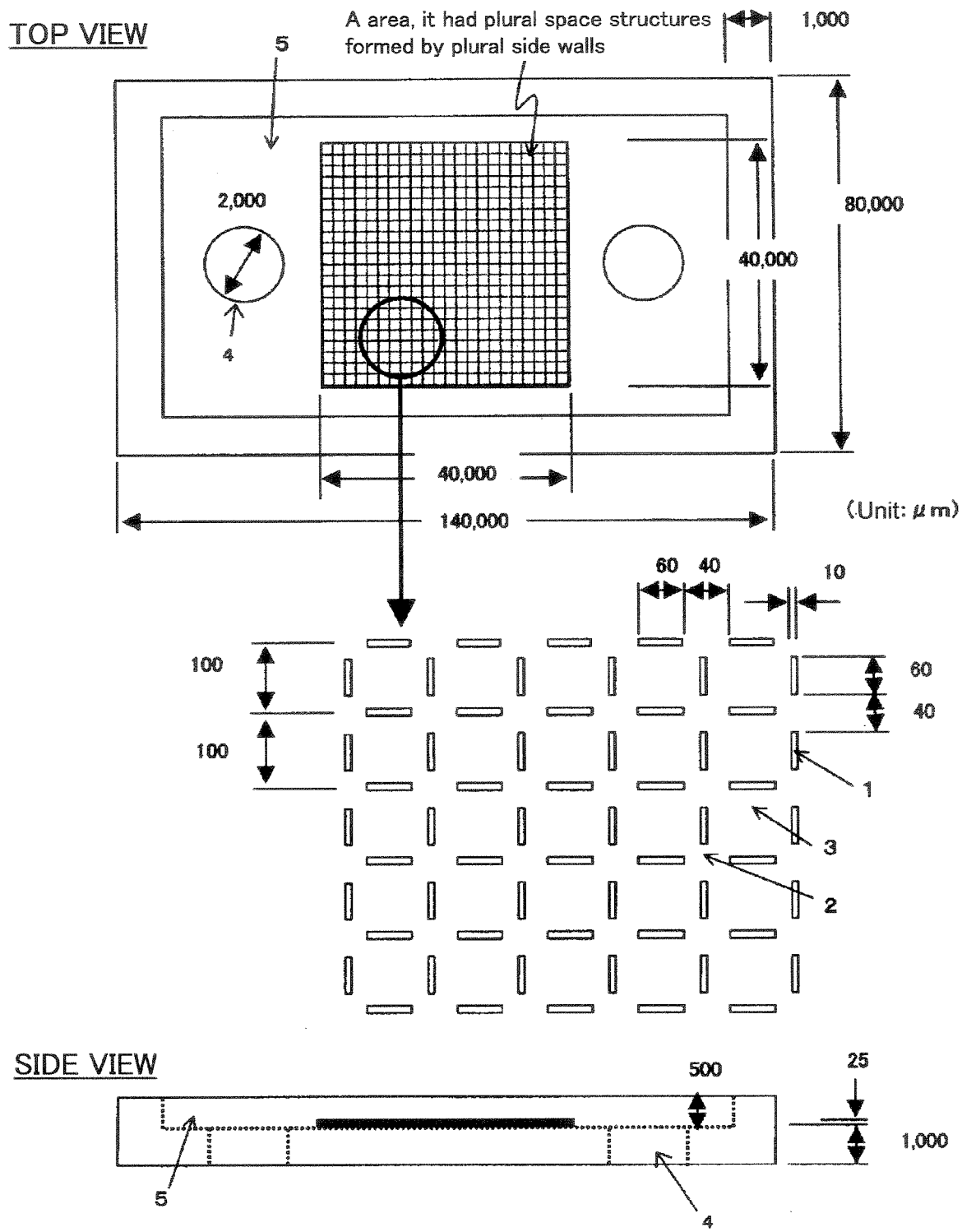
FIG. 4 A representation of a yet another example of the embodiment of the cell culture plate.

A resin-made cell culture plate (C) shown in FIG. 4 was produced by the same production method as the method of producing the resin-made cell culture plate A.

The external shape of the cell culture plate C was defined by a substrate having a length of 80 mm, a width of 140 mm and a thickness of 1 mm, and the central area, 40 mm in length×40 mm in width, was structured such that it had plural space structures formed by plural side walls, with two through-holes 4 with a diameter of 2 mm for the perfusion of a culture solution being disposed on both sides of that area. Each side wall 1 had a thickness of 10 μm, a height of 15 μm and a width of 60 μm, and each space structure 3, 100 μm in length×100 μm in width and 15 μm in height, was formed by four side walls. Each opening 2 for communicating the plurality of space structures was a space or gap between straightly arranged side walls in each of the longitudinal and transverse directions, with the side wall 1-to-side wall 1 distance being 40 μm.

In cell culture testing, the resin-made cell culture plate C is immersed in a culture solution and an acrylic plate is superimposed thereon, and the culture test is carried out in an environment such that the culture solution is circulated through the through-holes 4. The whole upper surface of the plurality of space structures constitutes a channel 5 for the culture solution to flow through the same, and the gap distance from the acrylic plate was 0.5 mm.

<Production of Cell Culture Plate D>

Figure 5:
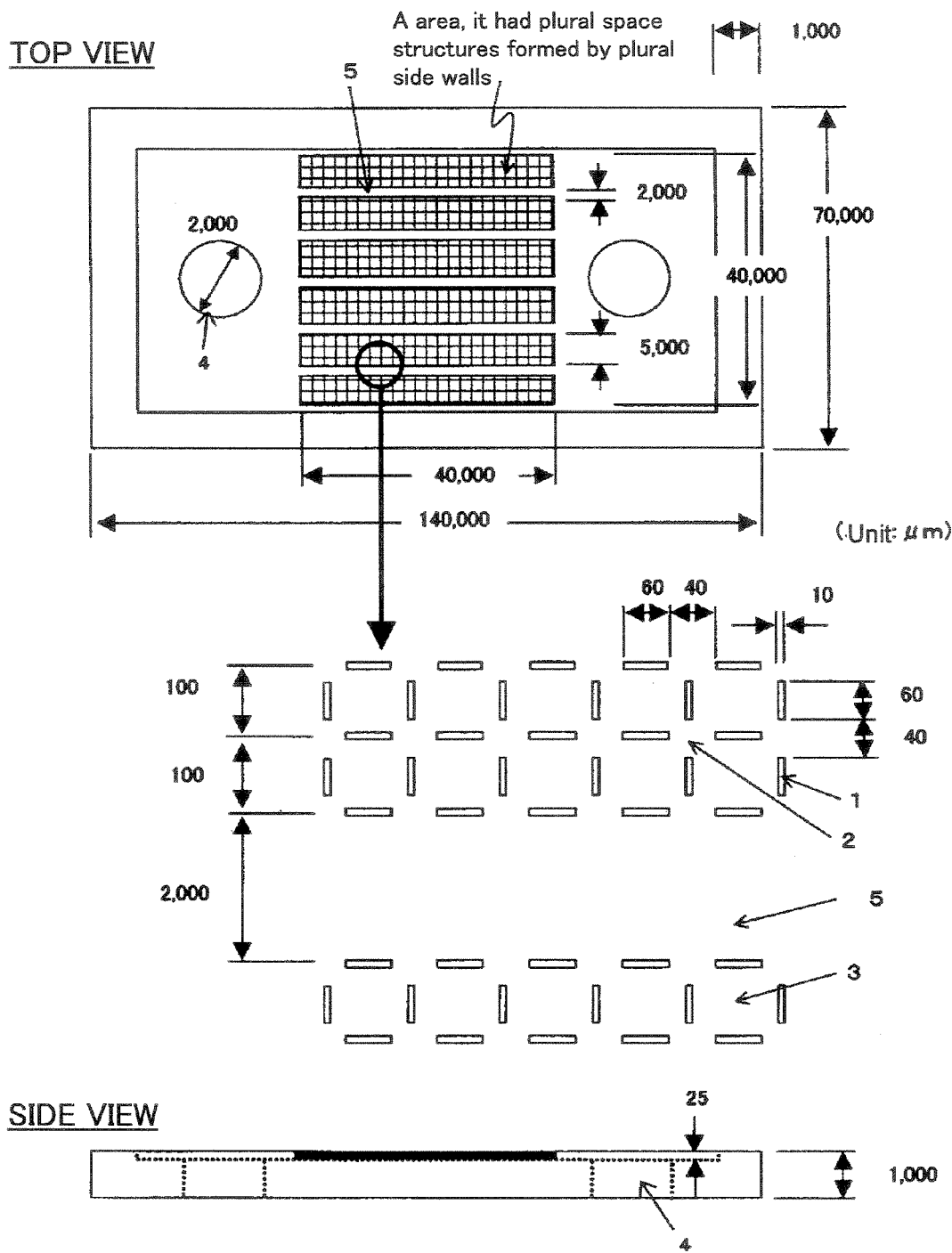
FIG. 5 A representation of a further example of the embodiment of the cell culture plate.

A resin-made cell culture plate (D) shown in FIG. 5 was produced by the same production method as the method of producing the resin-made cell culture plate A.

The external shape of the cell culture plate C was defined by a substrate having a length of 70 mm, a width of 140 mm and a thickness of 1 mm, and the central area, 40 mm in length×40 mm in width, was structured such that it had plural space structures formed by plural side walls 1, with two through-holes 4 with a diameter of 2 mm for the perfusion of a culture solution being disposed on both sides of that area. Each side wall 1 had a thickness of 10 μm, a height of 15 μm and a width of 60 μm, and each space structure 3, 100 μm in length×100 μm in width and 25 μm in height, was formed by four side walls 1. Each opening 2 for communicating the plurality of space structures was a space or gap between straightly arranged side walls in each of the longitudinal and transverse directions, with the side wall 1-to-side wall 1 distance being 40 μm.

In cell culture testing, the resin-made cell culture plate D is immersed in a culture solution and an acrylic plate is superimposed thereon, and the culture test is carried out in an environment such that the culture solution is circulated through the through-holes 4. Five channels 5, 2 mm in width and 40 mm in depth, were provided at regular intervals in the area provided with the plurality of space structures. The acrylic plate and the top of the plurality of space structures are in close contact with each other.

<Production of Cell Culture Plate E>

Figure 6:
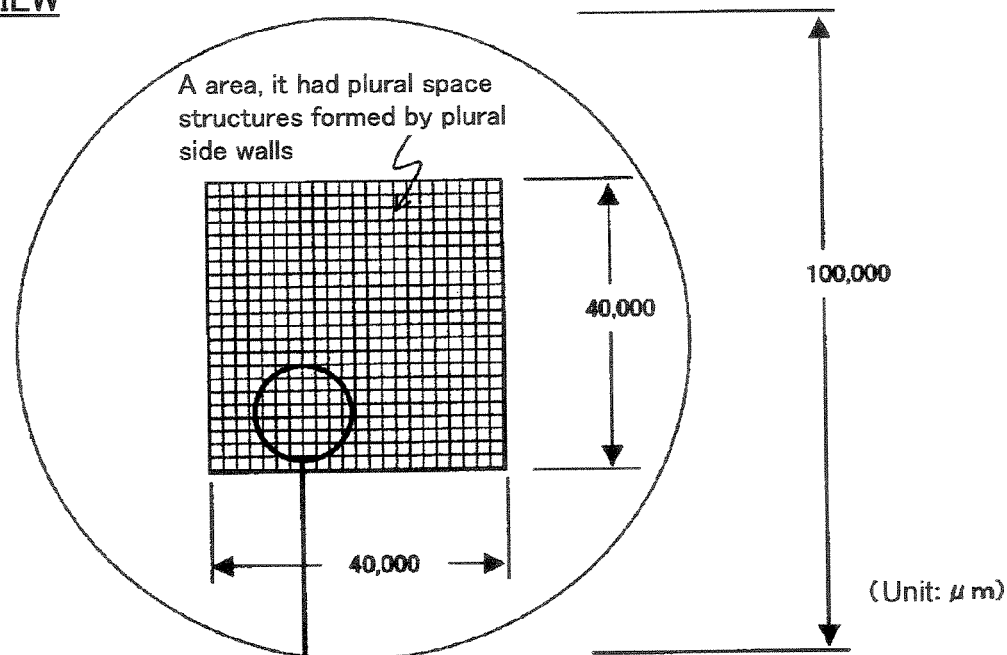
FIG. 6 A representation of a still further example of the embodiment of the cell culture plate.
Figure 6:
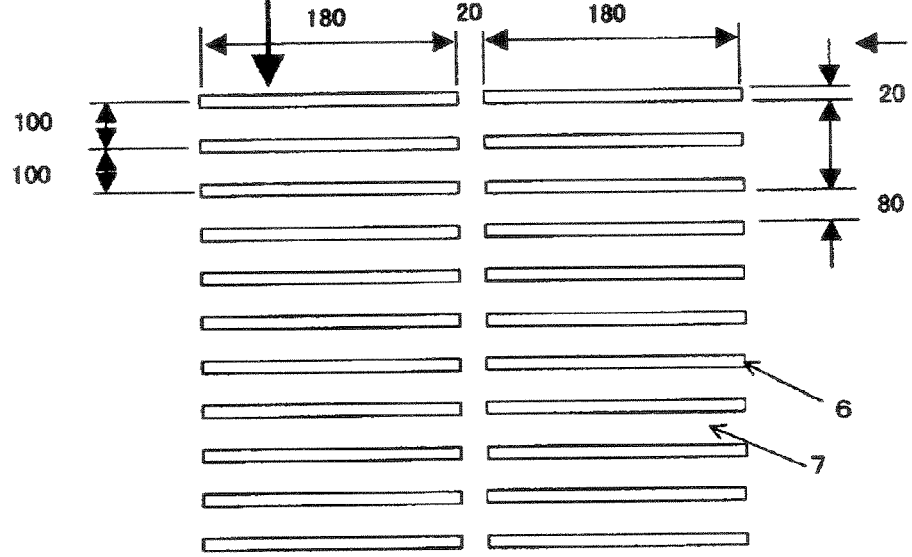
Figure 6:
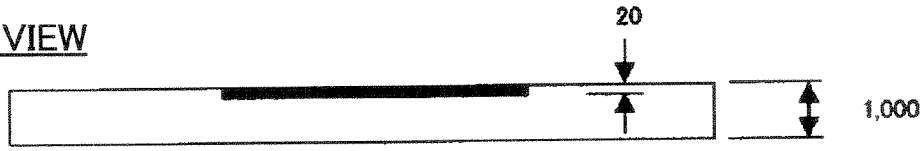

A resin-made cell culture plate (E) shown in FIG. 6 was produced by the same production method as the method of producing the resin-made cell culture plate A.

The external shape of the cell culture plate E was defined by a substrate having a diameter of 100 mm and a thickness of 1 mm, and the central area, 40 mm in length×40 mm in width, was structured such that it had plural concave patterns. Each concave pattern 6 had a width of 20 μm, a depth of 30 μm and a length of 180 μm, and the patterns showed a continuous structure at lengthwise intervals of 80 μm and transverse intervals of 20 μm.

<Preparation of Cell Culture Plates>
(Cell Culture Plates A to E)

The cell culture plates A to E were subjected to sterilization treatment by ultraviolet irradiation. Then, collagen promoting the adhesion of cells was applied thereto to prepare plates for culturing cells, and the plates were then fixed onto petri dishes.

(Comparative Culture Plates 1 and 2)

Slide glasses 1 and 2 were used and subjected to sterilization treatment by ultraviolet irradiation. Then, collagen promoting the adhesion of cells was applied thereto to prepare plates for culturing cells, and the plates were then fixed onto petri dishes.

<Cell Culture Environment on Cell Culture Plates>
(Cell Culture Plates A to D and Comparative Plate A)

Rat cardiac myocytes were distributed on the area provided with space structures of each of the cell culture plates A to D and on the comparative plate 1, followed by immersion in a culture solution. Simultaneously with the immersion in the culture solution, an acrylic plate was superimposed on each of the cell culture plates C and D, and the culture solution was circulated through the through-holes 4.

(Cell Culture Plate E and Comparative Plate B)

Rat bone marrow interstitial cells or chicken embryo fibroblasts prepared from rat bone marrow or chicken embryo heart, respectively, by isolation culture were distributed on the concave pattern area of the cell culture plate E and on the comparative culture plate 2, followed by immersion in a culture solution.

<Comparison Between Cell Cultures on Culture Plates>
(Cell Culture Plates A to D and Comparative Culture Plate 1)

Cell culture tests were carried out for 4 days under the conditions mentioned above. In the tests using the cell culture plates C and D, a fresh culture solution could always be fed, so that no culture solution exchange was carried out whereas, in the tests using the cell culture plates A and B and the comparative culture plate 1, culture solution exchange was made on the third day after the start of testing.

Three-dimensional growth of cardiac myocytes in the plurality of space structures 3 formed by the plurality of side walls 1 on the cell culture plates A to D was confirmed. Desmosomes to serve as pseudo-scaffolds for cardiac myocytes were formed on a side wall 1 and three-dimensionally grew in each space structure 3. And, the cardiac myocytes cultured in the space structure 3 formed desmosomes, namely pseudo-scaffolds, on the opposing side wall 1 as well. And, the cardiac myocytes cultured three-dimensionally in the respective space structures 3 were interconnected via the openings 2 and, as a result, cardiac muscle cell sheets with the extension direction regulated were successfully obtained. Each interconnected unit of the thus-obtained cardiac muscle cell sheets with the extension direction regulated pulsated synchronously and it was confirmed from the pulsation stroke that each sheet was reproducing the vital tissue.

It is expected that, in the future, a laminate made of the thus-obtainable cardiac muscle cell sheets under regulation of the extension direction may be applied to live tissue transplantation for the treatment for restoring normal function of the heart to thereby produce a therapeutic effect.

In the tests using the cell culture plates C and D, the above results could be obtained without any culture solution exchange. Such cell culture plates according to the invention are expected to be applicable even in the cases where cell culture is regarded as difficult, such as in hepatocyte culture, because a fresh culture solution is always fed and there is no fear of decreases in the activity of cultured cells due to waste materials discharged from cells and changes in pH, among others. The possibility of automated culture, for instance, is another advantage.

Figure 3:
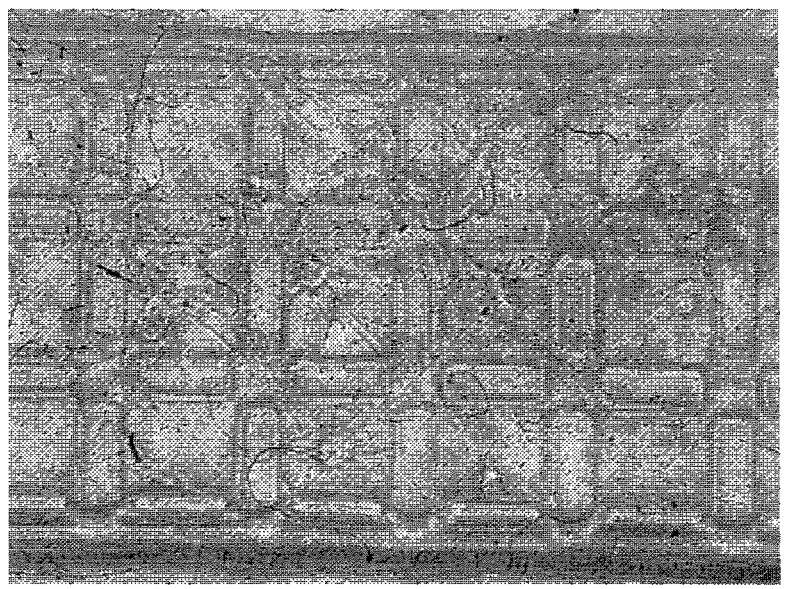
FIG. 3 A photograph of cells cultured using the cell culture plate shown in FIG. 1.

The result of culturing rat cardiac myocytes using the cell culture plate A is shown in the photograph in FIG. 3.

On the other hand, in the case of culture on the comparative culture plate 1, cultured cells extended thinly and failed to show a three-dimensional structure. Cells extended without any directionality and it was observed that the respective cardiac muscles on the plate were pulsating each individually. This result indicates that cultured cells showing no three-dimensional structure will not show the function they had in cells in vivo and, in addition, predicts that it is difficult to use them in assay test judgments since there is no directionality of extension of cardiac myocytes.

(Cell Culture Plate E and Comparative Culture Plate 2)

In the test using the cell culture plate E, rat bone marrow interstitial cells and chicken embryo fibroblasts were successfully cultured in the form regulated in the extension direction. It was confirmed that rat bone marrow interstitial cells and chicken embryo fibroblasts respectively formed desmosomes to serve as pseudo-scaffolds on the side wall of each concave pattern 6 or the top of each concave pattern 6 and then extended selectively toward the top of each concave which is the communicating surface 7, without extending to the inside of each concave pattern 6. Thus, the direction of extension of cultured cells is regulated in the direction along the communicating surface 7.

On the other hand, in the test using the comparative culture plate 2, cells extended thinly all over the slide glass; thus, the extension direction could not be regulated.

Whereas the culture surface on the slide glass could not have any gap or space, it is possible, using the cell culture plate E, to carry out the culture under control of the gaps on the culture surface by means of the concave patterns 6. It is expected that this technology makes it possible to carry out cell culture in a manner more precisely reproducing the corresponding living tissue by compositely combining cultured cells, for example by coculturing vascular endothelial cells.

The invention claimed is:

1. A method of culturing cardiac myocytes, comprising providing cardiac myocytes and culture medium to a cell culture plate and culturing the cardiac myocytes in the cell culture plate to form an interconnected cardiac muscle sheet which pulsated synchronously, wherein the cell culture plate comprises a plurality of concave or convex patterns and a surface communicating with the upper part of each concave or the bottom of each convex as a result of providing such concave or convex patterns to induce the formation of desmosomes, which serve as scaffolds in culture, on the communicating surface or on the side walls of each rugged pattern, whereby cells grow on the communicating surface where they can extend to regulate extension of the cultured cardiac myocytes, wherein the cardiac myocytes are distributed over the area of the plurality of concave or convex patterns and the surface communicating with the upper part of each concave or the bottom of each convex pattern.

2. The method according to claim 1, wherein the cell culture plate is surface-treated for cell immobilization.

3. The method according to claim 1, wherein the cell culture plate is made of a resin molding.

4. The method according to claim 1, wherein the cell culture plate is made of at least one material selected from the group consisting of an acrylic resin, poly(lactic acid), poly (glycolic acid), a styrenic resin, an acrylic-styrene copolymer, a polycarbonate, a polyethylene terephthalate, polyester, polyvinyl alcohol, ethylene-vinyl alcohol copolymer, styrenic elastomer, vinyl chloride, polydimethylsiloxane, vinyl acetate, and polyvinyl butyral resin.

5. A method of culturing cardiac myocytes, comprising
providing cardiac myocytes and culture medium to a cell culture plate and culturing the cardiac myocytes in the cell culture plate to form an interconnected cardiac muscle sheet which pulsated synchronously,
wherein the cell culture plate comprises a plurality of side walls and a plurality of space structures for arranging the cardiac myocytes which are formed by the plurality of side walls, wherein the plurality of side walls comprise openings configured to provide a communicative structure that allows communication of the plurality of space structures to thereby induce the formation of desmosomes, which serve as scaffolds in cell culture, on the side walls, whereby the cardiac myocytes cultured in each space structure extend toward the opposing side walls and the cardiac myocytes cultured in the respective space structures are connected through the openings that directionally regulates extension of the cultured cardiac myocytes,
wherein the cardiac myocytes are distributed over the area of the plurality of side walls and the plurality of space structures.

6. The method of culturing cells according to claim 5, wherein each side wall in the cell culture plate has a height of 3 μm to 1000 μm, a thickness of 3 μm to 1000 μm and a width of 3 μm to 3000 μm.

7. The method of culturing cells according to claim 6, wherein the cell culture plate comprises one or more channels for perfusing the culture medium.

8. The method of culturing cells according to claim 7, wherein the channel width is 1 μm to 1000 μm and the channel depth is 1 μm to 1000 μm.

9. The method of culturing cells according to claim 5, wherein the cell culture plate comprises one or more channels for perfusing the culture medium.

10. The method of culturing cells according to claim 9, wherein the channel width is 1 μm to 1000 μm and the channel depth is 1 μm to 1000 μm.

11. The method of culturing cells according to claim 5, wherein the cell culture plate comprises a fine uneven or rugged pattern with each projection or cavity being 0.001 μm to 50 μm in height or depth, respectively, within each space structure.

12. The method according to claim 5, wherein the cell culture plate is surface-treated for cell immobilization.

13. The method according to claim 5, wherein the cell culture plate is made of a resin molding.

14. The method according to claim 13, wherein the resin molding is a water-soluble resin molding.

15. The method according to claim 3, wherein the resin molding is a water-soluble resin molding.

16. The method according to claim 5, further comprising culturing the cardiac myocytes in a plurality of cell culture plates that are laminated to each other.

17. The method according to claim 5, further comprising culturing the cardiac myocytes in a plurality of cell culture plates that are laminated to each other.

18. The method according to claim 5, wherein the plurality of side walls are rectangular in shape.

19. The method according to claim 5, wherein the cell culture plate is made of at least one material selected from the group consisting of an acrylic resin, poly(lactic acid), poly (glycolic acid), a styrenic resin, an acrylic-styrene copolymer, a polycarbonate, a polyethylene terephthalate, polyester, polyvinyl alcohol, ethylene-vinyl alcohol copolymer, styrenic elastomer, vinyl chloride, polydimethylsiloxane, vinyl acetate, and polyvinyl butyral resin.

* * * * *